(12) United States Patent
Mei et al.

(10) Patent No.: US 6,498,643 B1
(45) Date of Patent: Dec. 24, 2002

(54) SPHERICAL SURFACE INSPECTION SYSTEM

(75) Inventors: Wenhui Mei, Plano, TX (US); Bright Qi, Plano, TX (US); Bei Chen, Plano, TX (US)

(73) Assignee: Ball Semiconductor, Inc., Allen, TX (US)

( * ) Notice: Subject to any disclaimer, the term of this patent is extended or adjusted under 35 U.S.C. 154(b) by 150 days.

(21) Appl. No.: 09/711,626

(22) Filed: Nov. 13, 2000

(51) Int. Cl.$^7$ .............................................. G01N 21/01
(52) U.S. Cl. ...................................................... 356/244
(58) Field of Search ................................ 356/244, 246, 356/358, 360, 345, 237.1, 237.2, 237.3, 237.4, 237.5; 250/572, 562, 563

(56) References Cited

U.S. PATENT DOCUMENTS

| | | | |
|---|---|---|---|
| 3,521,350 A | 7/1970 | Knippenberg et al. | 29/572 |
| 3,534,467 A | 10/1970 | Sachs et al. | 29/583 |
| 3,593,191 A | 7/1971 | Henker | 331/94.5 |
| 3,988,232 A | 10/1976 | Wasa et al. | 204/192 |
| 3,998,659 A | 12/1976 | Wakefield | 136/89 |
| 4,094,751 A | 6/1978 | Nozik | 204/80 |
| 4,100,051 A | 7/1978 | Kilby et al. | 204/266 |
| 4,100,422 A | 7/1978 | Thillays | 250/551 |
| 4,126,812 A | 11/1978 | Wakefield | 313/500 |
| 4,136,436 A | 1/1979 | Kilby et al. | 29/572 |
| 4,152,712 A | 5/1979 | Myers | 357/17 |
| 4,173,494 A | 11/1979 | Johnson et al. | 136/89 |
| 4,270,263 A | 6/1981 | Johnson et al. | 29/590 |
| 4,407,320 A | 10/1983 | Levine | 136/250 |
| 4,451,968 A | 6/1984 | Jensen et al. | 29/572 |
| 4,548,658 A | 10/1985 | Cook | 148/175 |
| 4,555,635 A | * 11/1985 | Yoshida | 250/572 |
| 4,614,835 A | 9/1986 | Carson et al. | 136/250 |
| 4,637,855 A | 1/1987 | Witter et al. | 156/616 |
| 4,806,495 A | 2/1989 | Levine et al. | 437/2 |
| 4,834,856 A | 5/1989 | Wehner | 204/192.24 |
| 4,879,466 A | 11/1989 | Kitaguchi et al. | 250/370.14 |
| 4,952,425 A | 8/1990 | Allen et al. | 427/213 |

(List continued on next page.)

FOREIGN PATENT DOCUMENTS

| | | |
|---|---|---|
| JP | 5921082 | 5/1984 |
| JP | 284499 | 10/1993 |
| JP | 302799 | 11/1994 |

OTHER PUBLICATIONS

Nakata, *Gravity–Dependent Silicon Crystal Growth Using a Laser Heating System in Drop Shaft*, Sep. 1, 1994, pp. L1202–L1204.

*Primary Examiner*—Michael P. Stafira
(74) *Attorney, Agent, or Firm*—Haynes & Boone LLP

(57) ABSTRACT

Method and apparatus are described for a spherical surface inspection system comprising a controller having software, an optical sensor connected to the controller, and an inspection device disposed adjacent to the optical sensor, and connected to the controller. The inspection device is for retaining and rotating the spherical-shaped object along a first axis to allow the optical sensor to convey an image of a portion of the surface of the spherical-shaped object to the controller. The inspection device also rotates the spherical-shaped object along a second axis to convey an image of more of the surface of the spherical-shaped object to the controller.

28 Claims, 4 Drawing Sheets

U.S. PATENT DOCUMENTS

| | | | |
|---|---|---|---|
| 5,028,546 A | 7/1991 | Hotchkiss | 437/2 |
| 5,069,740 A | 12/1991 | Levine et al. | 156/616.2 |
| 5,081,519 A | 1/1992 | Nishimura | 357/60 |
| 5,086,003 A | 2/1992 | Hammerbacher | 437/2 |
| 5,106,455 A | 4/1992 | Jacobsen et al. | 156/659.1 |
| 5,131,976 A | 7/1992 | Hoko | 156/630 |
| 5,269,882 A | 12/1993 | Jacobsen | 156/659.1 |
| 5,278,097 A | 1/1994 | Hotchkiss et al. | 437/164 |
| 5,358,603 A | 10/1994 | Ibrahim et al. | 156/657 |
| 5,361,272 A | 11/1994 | Gorelik | 372/50 |
| 5,382,412 A | 1/1995 | Kim et al. | 422/142 |
| 5,405,658 A | 4/1995 | Ibrahim et al. | 427/588 |
| 5,431,127 A | 7/1995 | Stevens et al. | 117/75 |
| 5,457,333 A | 10/1995 | Fukui | 257/253 |
| 5,466,301 A | 11/1995 | Hammerbacher et al. | 136/246 |
| 5,546,417 A | 8/1996 | Gorelik | 372/36 |
| 5,588,993 A | 12/1996 | Holder | 117/13 |
| 5,659,184 A | 8/1997 | Tokunaga et al. | 257/91 |
| 5,703,687 A * | 12/1997 | Kumagai et al. | 356/426 |
| 5,777,244 A * | 7/1998 | Kumagai et al. | 73/865.8 |
| 5,905,575 A * | 5/1999 | Matsuoka | 356/359 |
| 5,955,776 A | 9/1999 | Ishikawa | 257/618 |

* cited by examiner

SPHERICAL SURFACE INSPECTION SYSTEM

This application pertains to an inspection system for the surfaces of spherical-shaped objects.

DETAILED DESCRIPTION

Figure 1:
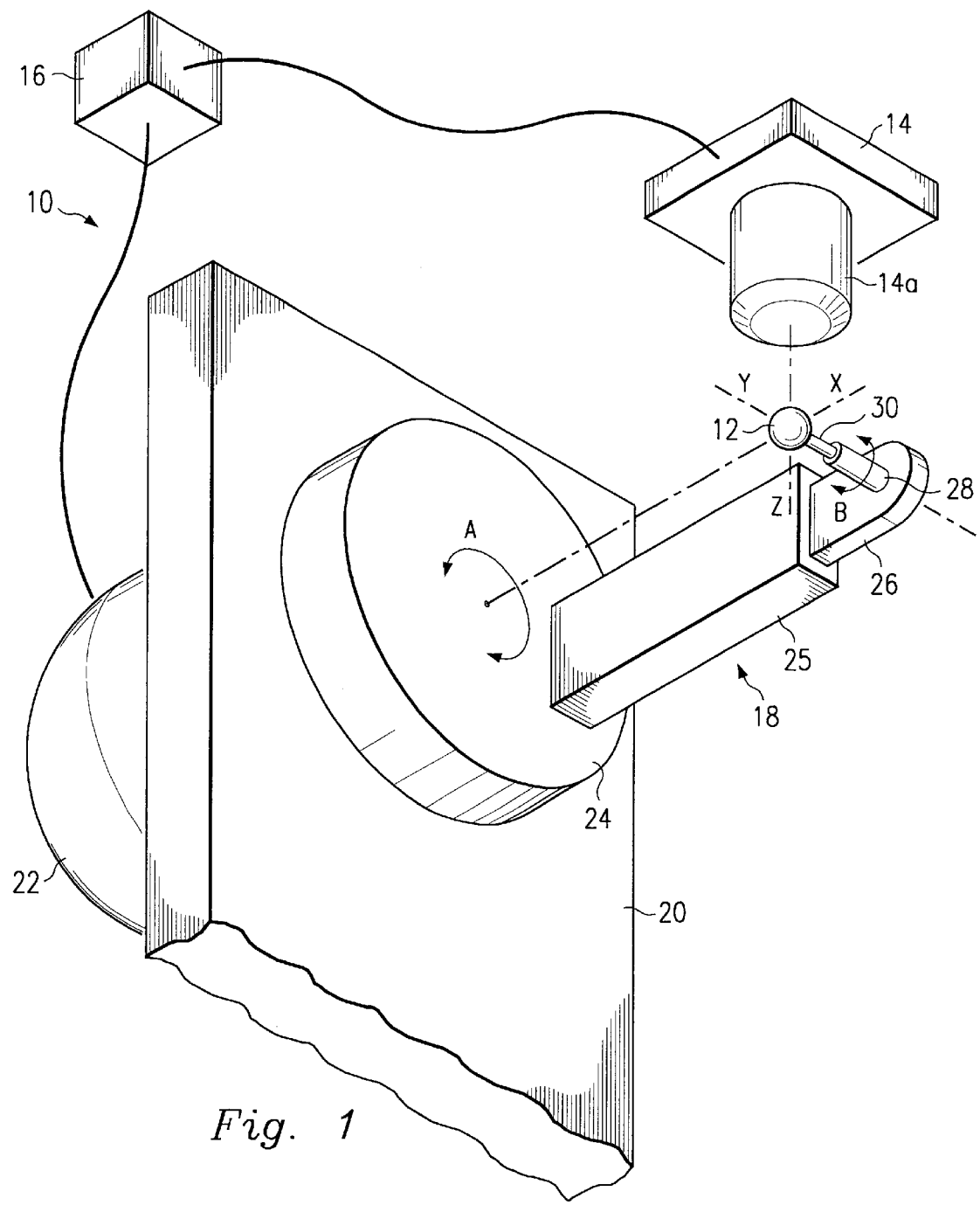
FIG. 1 is a perspective view of an inspection system according to the present embodiment.

FIG. 1 depicts a system 10 for allowing inspection of a spherical-shaped object 12. Although many uses are contemplated for the system 10, in an illustrative embodiment, the spherical-shaped object 12 is a spherical-shaped semiconductor, the term "semiconductor" being used without consideration for the particular stage of manufacturing or processing steps in which inspection occurs. Generally, a substrate is used to form an orb, and an alignment mark is provided on the surface of the orb. All subsequent lithographic and etching processes are aligned to the alignment mark, and hence to each other, to eventually produce the final product, a spherical-shaped semiconductor integrated circuit. It is desirable to inspect the surface of the semiconductor occasionally during manufacture and processing.

An optical sensor 14 is provided for conveying an image of the spherical-shaped object 12. The optical sensor 14 has a lens 14a, for example, a conventional 5×, 10×, 20×, 25×, or a 50× objective lens, the power of the lens depending on the desired resolution. The optical sensor 14 is operably connected to a controller 16, which comprises software and connectors necessary to observe and control manipulation of the spherical-shaped object 12, in a manner to be explained.

An inspection device, generally referred to by the reference numeral 18, is connected to the controller 16 and retains the spherical-shaped object 12. The device 18 has a housing 20, with a motor 22 attached to the housing. The motor 22 produces rotary motion when prompted by the controller 16. The motor 22 is attached to a stage 24, which rotates equatorially, as indicated by the reference arrow A.

An arm 25 is affixed to the stage 24, extending outwardly relative to the stage. A retainer 26 is disposed on the arm 25, and retains a sleeve 28. A rod 30 is rotatably disposed in the sleeve 28, as indicated by the reference arrow B. The rod 30 is connected to conventional means for producing the rotation B, such as a small motor (not depicted) disposed in the retainer 26, arm 25, or stage 24, or alternatively, to gears operably connected to the motor 22. It is understood that the spherical-shaped object 12 may be removably coupled to the rod 30 by any of various means, such as by a vacuum produced in a cavity (not depicted) of the rod to draw the spherical-shaped object to the rod, or by reversibly affixing the spherical-shaped object to the rod.

As depicted, the position of the spherical-shaped object 12 is reflected by three illustrative axes, X, Y, and Z. The X axis runs from the center of the stage 24 through the center of the spherical-shaped object 12. Thus, rotation A is around the X axis. The Y axis runs through the center of the rod 30 and the spherical-shaped object 12, and thus, rotation B is around the Y axis. The Z axis runs through the center of the lens 14a and the spherical-shaped object 12. Once retained by the rod 30, the spherical-shaped object 12 moves with the stage 24, arm 25, and rod during rotation A. The rod 30 also imparts its rotation B to the spherical-shaped object 12.

The controller 16 controls the amount and sequence of rotation A and the rotation B, and hence respective corresponding rotations of the spherical-shaped object 12, as will be described. The rotation B may occur simultaneously, or separately, from rotation A above, and a number of rotational ratios (degrees A:degrees B) are contemplated. It is understood that rotation A and rotation B could each occur in two rotational directions, clockwise or counterclockwise. Additionally, the net rotation produced on the spherical-shaped object 12 in the desired rotational direction (rotation A or rotation B) depends on the duration of rotation.

Figure 2:
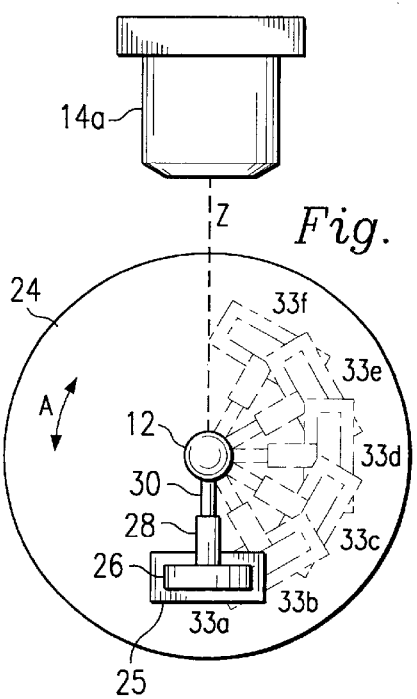
FIG. 2 is a plan view of a portion of a device for rotating a spherical-shaped object according to the system of FIG. 1.

For example, and referring now to FIG. 2, the stage 24 may be rotated in rotation A, counterclockwise as depicted from arm position 33a, to produce a set of illustrative arm positions 33b–f, shown in phantom, representing an infinite set of possible arm positions. It is understood that each of the arm positions 33b–f is produced by a different net rotational duration, increasing respectively, from the arm position 33a. Alternatively, the rotation A could occur in the opposite direction (clockwise).

Figure 3A:
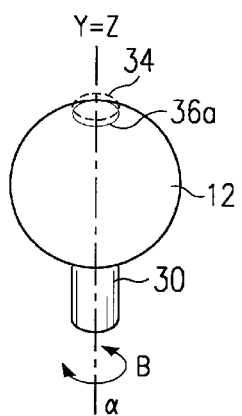
FIGS. 3a–f are schematic views of the spherical-shaped object at several points during inspection.

Each of the arm positions 33a–f is associated with a unique orientation of the spherical-shaped object 12 with respect to the Z axis, as illustrated in FIGS. 3a–f, respectively. More specifically, and referring to FIGS. 3a–f, the counterclockwise rotation A (FIG. 2) moves the Y axis (aligned with the rod 30) in relation the Z axis. Thus, the rotation A (FIG. 2) produces a set of increasing angular displacements $\alpha$, $\beta$, $\gamma$, $\delta$, $\epsilon$, and $\lambda$, between the Y and Z axes for the respective positions 33a–f. For example, as shown in FIG. 3a, the angular displacement of a (position 33a of FIG. 2) is approximately zero degrees. It is understood that the field of view 34 (represented by the dashed circle) of the lens 14a (FIG. 1) is normally concentric to the Z axis, and that an angular displacement of approximately zero causes the field of view 34 to be disposed on the surface of the spherical-shaped object 12 concentric to the Y axis as well.

Figure 3B:
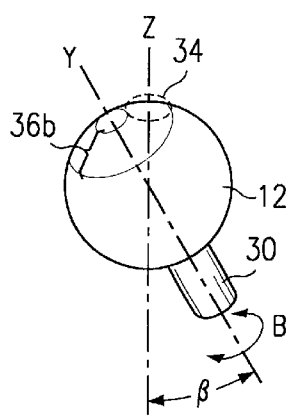
Figure 3C:
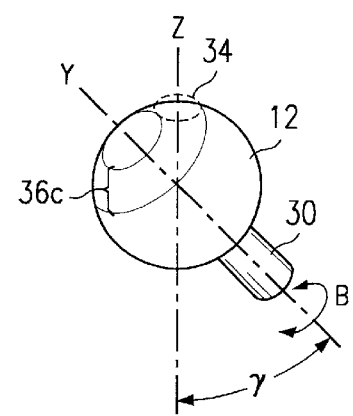
Figure 3D:
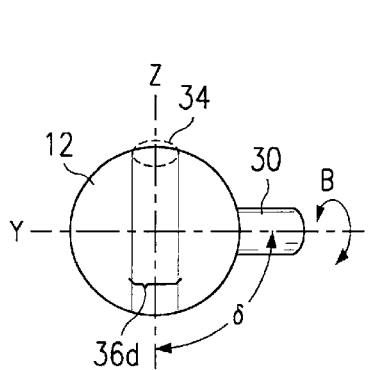
Figure 3E:
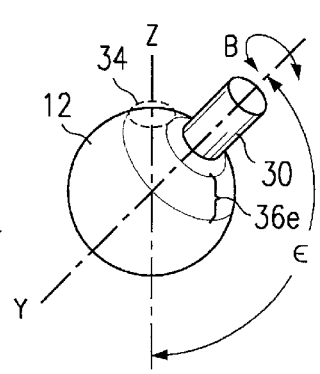
Figure 3F:
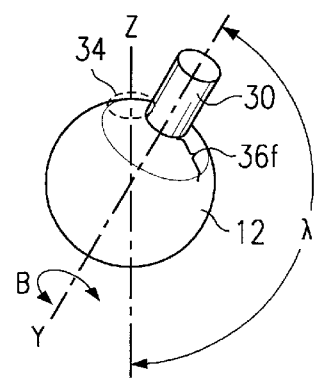

Turning to FIG. 3b, rotation A produces an angular displacement $\beta$ between the Y and Z axes. A 360° rotation B of the rod 30 will move the field of view 34 in a path of a predetermined area ("loop") 36b around the surface of the spherical-shaped object 12. Loops for the for the angular displacements $\alpha$, $\beta$, $\gamma$, $\delta$, $\epsilon$, and $\lambda$, have been given the reference numerals 36a–f, respectively, although it is understood that loop 36a is equivalent to the field of view 34.

TABLE 1

| Rotation A<br>Angular displacement of Y axis<br>relative to Z axis | Rotation B<br>Degrees | Loop |
| --- | --- | --- |
| α | — | 36a |
| β | 360° rotation | 36b |
| γ | 360° rotation | 36c |
| δ | 360° rotation | 36d |
| ε | 360° rotation | 36e |
| λ | 360° rotation | 36f |

The angular displacements α, β, γ, δ, ε, and λ, are selected in a manner to allow the loops 36a–f to abut, or alternatively, to overlap, each other, and it is understood that in practice, the number of loops required depends upon the width of the field of view 34 in relation to the surface area of the spherical-shaped object 12 to be covered.

Figure 4:
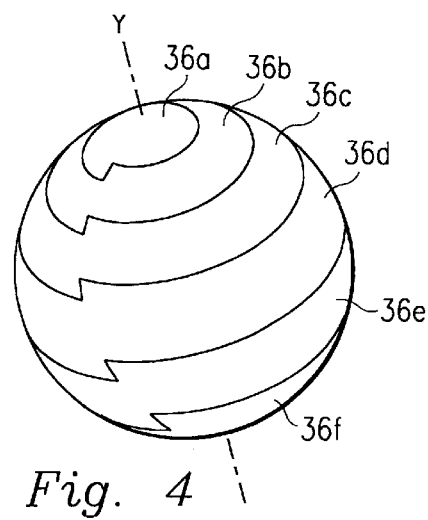
FIG. 4 is a schematic view of the inspection path on the spherical-shaped object.

In operation, referring to FIG. 4, the controller 16 (FIG. 1) plots and executes a series of combinations for rotations A and B, thereby moving the len's field of view 34 (FIGS. 3a–f) in the loops 36a–f over the surface of the spherical-shaped object 12. As such, the lens 14a, and hence the controller 16, observes the surface of the spherical-shaped object 12 disposed in each of the loops 36a–f.

Images of the spherical-shaped object 12 (observed as the loops 36a–f) may be stored and/or combined to form a software-generated image of the surface of the spherical-shaped object. The software-generated image may be inspected by a user and/or by software for compliance with accepted appearance standards, such as for particles, scratches, and other defects. The software-generated image may also be manipulated for analysis, such as moved, rotated, or zoomed. Moreover, the spherical-shaped object may retain an identifying area, such as a bar-code, which may be observed as well for identifying the spherical-shaped object 12.

In this manner, the entire surface of the spherical-shaped object 12 may be inspected, with the exception of the portion of the spherical-shaped object coupled to the end of the rod 30, which is understandably obscured. It is understood that the aforesaid obscured portion could be deemed unnecessary to inspect, or alternatively, the spherical-shaped object 12 could be detached from the rod 30 and recoupled at a different portion of the surface of the spherical-shaped object.

Although the rotations A and B have been discussed as occurring discretely for purposes of explanation, it is understood that the rotations A and B could occur incrementally and simultaneously to form a gradual spiral path around the surface of the spherical-shaped object 12.

Figure 5:
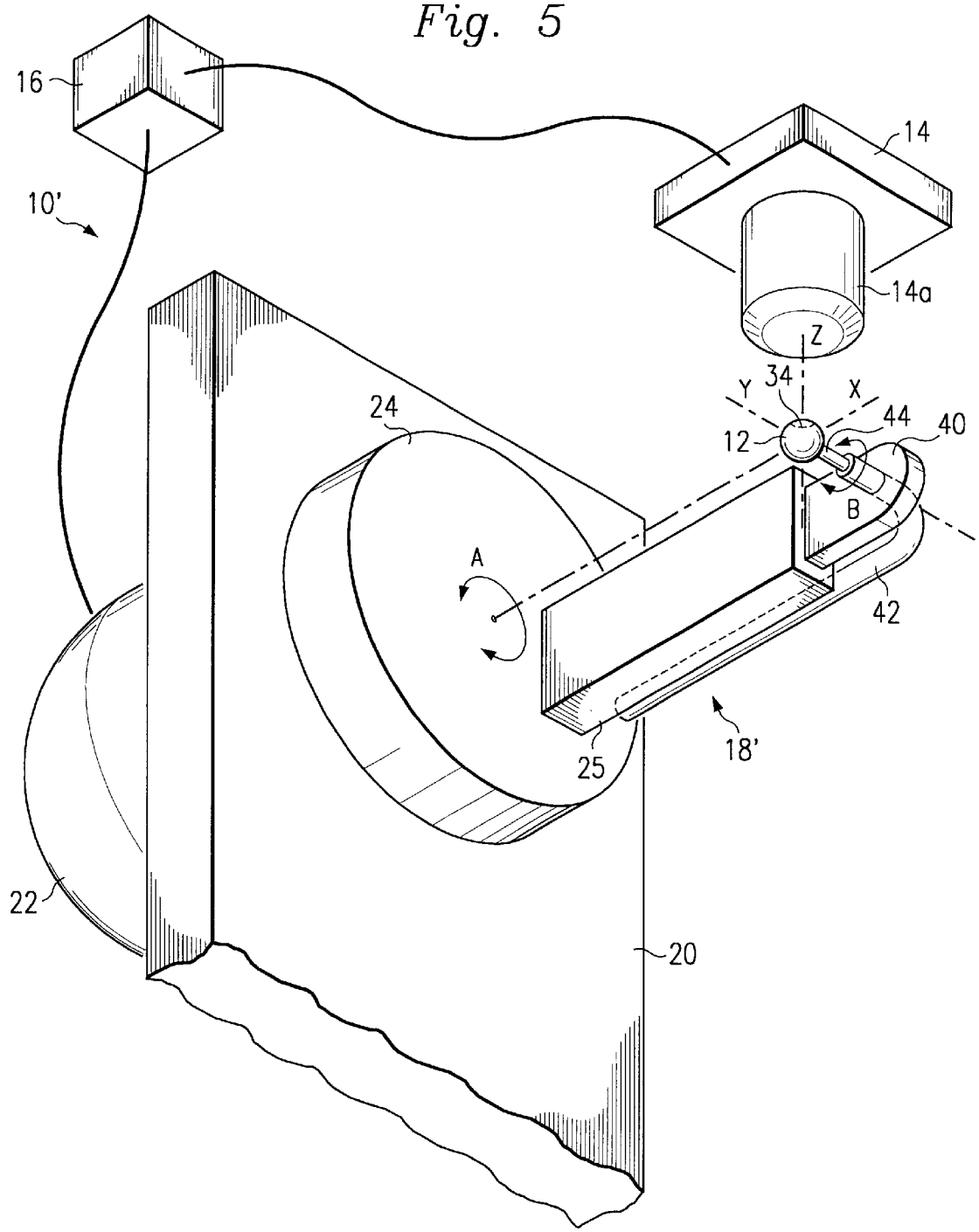
FIG. 5 is a perspective view of an alternative embodiment of the inspection system.

Referring to FIG. 5, a system 10' is depicted for allowing inspection of the spherical-shaped object 12. It is understood that the system 10' enjoys some of the same components as the foregoing embodiment of FIGS. 1–4, and thus, the reference numbers associated with those components are retained.

An optical sensor 14 is provided for conveying an image of the spherical-shaped object 12. The optical sensor 14 has a lens 14a, and is operably connected to a controller 16, which comprises software and connectors necessary to observe and control manipulation of the spherical-shaped object 12, in a manner to be explained.

An inspection device, generally referred to by the reference numeral 18', is connected to the controller 16 and retains the spherical-shaped object 12. The device 18' has a housing 20, with a motor 22 attached to the housing. The motor 22 produces rotary motion when prompted by the controller 16. The motor 22 is attached to a stage 24, which rotates equatorially, as indicated by the reference arrow A.

An arm 25 is affixed to the stage 24, extending outwardly relative to the stage. An extension 40 extends from the arm 25 to capture a sleeve 42. The sleeve 42 is somewhat flexible, but fixed by the extension 40. A tube 44 is rotatably disposed in the sleeve 42, as indicated by the reference arrow B. The tube 44 is connected to conventional means for producing the rotation B, such as a small motor (not depicted) disposed in the arm 25 or stage 24, or alternatively, to gears operably connected to the motor 22. It is understood that the tube 44 may be lubricated to facilitate the rotation B. As with the foregoing embodiment, the position of the spherical-shaped object 12 is reflected by three illustrative axes, X, Y, and Z. Rotation A is around the X axis, and rotation B is around the Y axis. The Z axis runs through the center of the lens 14a and the spherical-shaped object 12.

Figure 6:
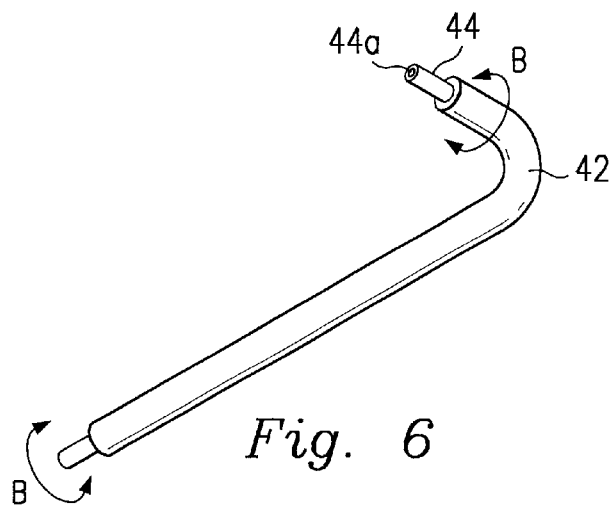
FIG. 6 is a perspective view of a sleeve and tube according to FIG. 5.

Referring to FIG. 6, the tube 44 is hollow, having an opening 44a. It is understood that the spherical-shaped object 12 may be removably coupled to the tube 44 by any of various means, such as by a vacuum produced in the opening 44a of the tube to draw the spherical-shaped object to the tube. Returning to FIG. 5, a vacuum producing device (not depicted) is understood to be operably connected to the tube 44 in such an embodiment.

Once retained by the tube 44, the spherical-shaped object 12 moves with the stage 24, arm 25, and tube during rotation A. The tube 44 also imparts its rotation B to the spherical-shaped object 12. The controller 16 controls the amount and sequence of rotation A and the rotation B, and hence respective corresponding rotations of the spherical-shaped object 12. The rotation B may occur simultaneously, or separately, from rotation A above, and a number of rotational ratios (degrees A:degrees B) are contemplated. It is understood that rotation A and rotation B could each occur in two rotational directions, clockwise or counterclockwise. Additionally, the net rotation produced on the spherical-shaped object 12 in the desired rotational direction (rotation A or rotation B) depends on the duration of rotation.

It is understood that the field of view 34 (represented by the dashed circle) of the lens 14a is normally concentric to the Z axis. As described in detail for the foregoing embodiment, rotation A produces a set of angular displacements between the Y and Z axes. A 360° rotation B of the tube 44 will then move the field of view 34 in a loop around the surface of the spherical-shaped object 12. The set of angular displacements are selected to allow the corresponding loops to abut, or alternatively, to overlap, each other.

In operation, the controller 16 plots and executes a series of combinations for rotations A and B, thereby moving the len's field of view 34 in the loops over the surface of the spherical-shaped object 12. As such, the lens 14a, and hence the controller 16, observes the surface of the spherical-shaped object 12. The images of the surface of the spherical-shaped object 12 observed via the loops may be stored and/or combined, and may be inspected by a user and/or by software for compliance with accepted appearance standards. In this manner, the entire surface of the spherical-shaped object 12 may be inspected, with the exception of the portion of the spherical-shaped object coupled to the end of the tube 44, which is understandably obscured. It is understood that the aforesaid obscured portion could be deemed unnecessary to inspect, or alternatively, the spherical-shaped object 12 could be detached from the tube 44 and recoupled at a different portion of the surface of the spherical-shaped object.

Figure 7:
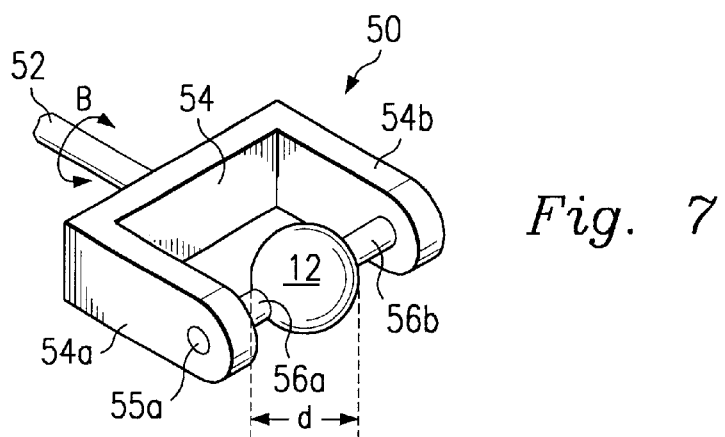
FIG. 7 is a perspective view of an alternative embodiment of a holding arm.

Referring to FIG. 7, a holder, generally referred to by the reference numeral 50, is depicted for allowing inspection of the spherical-shaped object 12. The holder 50 has an extension 52 which is understood to connect with the sleeve 28 (FIG. 1) or sleeve 42 (FIG. 5) of the foregoing systems, respectively 10 and 10', and to rotate in rotation B. The extension 52 is attached to a substantially U-shaped bracket 54, having arms 54a–b. Openings 55a–b are disposed in the bracket arms 54a–b, respectively, for receiving pins 56a–b.

The pins 56a–b have a distance d between the distal ends of the pins, the distance d being adjustable in an axial direction relative to the pins. The pins 56a–b capture and retain the spherical-shaped object 12. It can be appreciated that the pins 56a–b could capture spherical objects of varying diameters (not depicted) by appropriately adjusting the distance d between the distal ends of the pins.

Once installed in the sleeve of the system 10 or 10', the holder 50 retains the spherical-shaped object 12 to allow inspection of the spherical-shaped object in a manner previously described.

Figure 8:
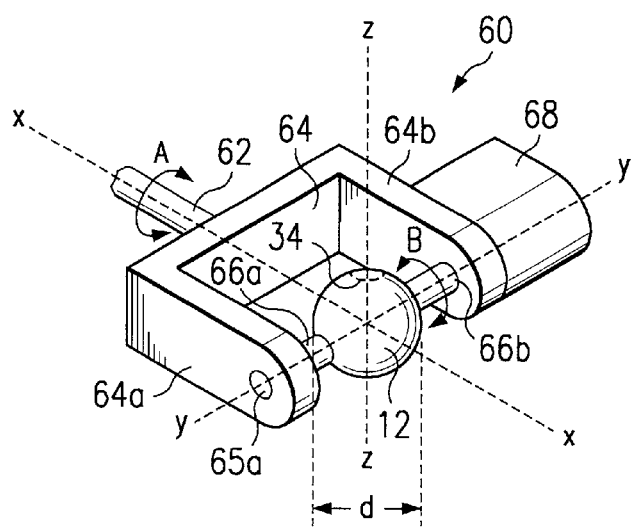
FIG. 8 is a perspective view of yet another alternative embodiment of a holding arm.

Referring to FIG. 8, an alternative embodiment of the holder of FIG. 7, generally referred to by the reference numeral 60, is depicted for allowing inspection of the spherical-shaped object 12. The holder 60 has an extension 62 which is understood to connect with the motor 22 (FIGS. 1 and 5) of the foregoing systems, respectively 10 and 10', and to rotate in rotation A. Thus, the stage 24 of the previous embodiments is removed, and hence the associated structure, such as arm 25, is removed as well. The X axis is aligned with the extension 62 and passes through the center of the spherical-shaped object 12.

The extension 62 is attached to a substantially U-shaped bracket 64, having arms 64a–b. Openings 65a–b are disposed in the bracket arms 64a–b, respectively, for receiving pins 66a–b. The pins 66a–b have a distance d between the distal ends of the pins, the distance d being adjustable in an axial direction relative to the pins. The pins 66a–b capture and retain the spherical-shaped object 12, and are rotatable along the Y axis to produce rotation B. At least one of the pins, for example 66b, is connected to conventional means for producing the rotation B, schematically represented as 68. It can be appreciated that the pins 66a–b could capture spherical objects of varying diameters (not depicted) by appropriately adjusting the distance d between the distal ends of the pins.

It is understood that the field of view 34 (represented by the dashed circle) of the lens 14a (FIGS. 1 and 5) is normally concentric to the Z axis. As described in detail for the foregoing embodiments, rotation A produces a set of angular displacements between the Y and Z axes. A 360° rotation B of the pins 66a–b will then move the field of view 34 in a loop around the surface of the spherical-shaped object 12. The set of angular displacements are selected to allow the corresponding loops to abut, or alternatively, to overlap, each other.

In operation, the controller 16 (FIGS. 1 and 5) plots and executes a series of combinations for rotations A and B, thereby moving the len's field of view 34 in the loops over the surface of the spherical-shaped object 12. As such, the lens 14a, and hence the controller 16, observes the surface of the spherical-shaped object 12. The images of the surface of the spherical-shaped object 12 observed via the loops may be stored and/or combined, and may be inspected by a user and/or by software for compliance with accepted appearance standards, as described above, with reference to the foregoing embodiments.

It is understood that all spatial references are for the purpose of example only and are not meant to limit the invention. Furthermore, this disclosure shows and describes illustrative embodiments, however, the disclosure contemplates a wide range of modifications, changes, and substitutions. Such variations may employ only some features of the embodiments without departing from the scope of the underlying invention. For example, other means of actuation are possible. Accordingly, any appropriate construction of the claims will reflect the broad scope of the underlying invention.

What is claimed is:

1. A system for inspecting the surface of a spherical-shaped object, the system comprising:

a controller having software;

an optical sensor connected to the controller; and an inspection device disposed adjacent to the optical sensor, and connected to the controller, the inspection device having means for retaining and rotating the spherical-shaped object along a first axis to allow the optical sensor to convey an image of a portion of the surface of the spherical-shaped object to the controller;

wherein the image includes an alignment mark.

2. The system of claim 1 wherein the inspection device also rotates the spherical-shaped object along a second axis to convey an image of more of the surface of the spherical-shaped object to the controller.

3. The system of claim 1 wherein the inspection device comprises:

a housing;

a motor attached to the housing for producing rotary motion; and means for retaining the spherical-shaped object, the means being attached to the motor to rotate the spherical-shaped object.

4. A system for inspecting the surface of a spherical-shaped object, the system comprising:

a controller having software;

an optical sensor connected to the controller; and an inspection device disposed adjacent to the optical sensor, and connected to the controller, the inspection device having means for retaining and rotating the spherical-shaped object along a first axis to allow the optical sensor to convey an image of a portion of the surface of the spherical-shaped object to the controller, wherein the inspection device comprises a housing, a motor attached to the housing for producing rotary motion, means for retaining the spherical-shaped object, the means being attached to the motor to rotate the spherical-shaped object, a stage attached to the motor and rotatable along the first axis, an arm extending from the stage, and a rod attached to the arm and rotatable along a second axis, the rod being removably coupled to the spherical-shaped object.

5. The system of claim 4 wherein the rod is retained in a sleeve.

6. The system of claim 5 wherein the sleeve is flexible.

7. The system of claim 3 wherein the inspection device further comprises a holder attached to the motor and rotatable along a first axis, and having at least one adjustable pin rotatable along a second axis, the pin being removably coupled to the spherical-shaped object.

8. The system of claim 7 wherein the at least one adjustable pin retains the spherical-shaped object by trapping the spherical-shaped object against another pin disposed in the holder.

9. A system for inspecting the surface of a spherical-shaped object, the system comprising:
- a controller having software;
- an optical sensor connected to the controller; and
- an inspection device disposed adjacent to the optical sensor, and connected to the controller, the inspection device having means for retaining and rotating the spherical-shaped object along a first axis to allow the optical sensor to convey an image of a portion of the surface of the spherical-shaped object to the controller, wherein the inspection device comprises a housing, a motor attached to the housing for producing rotary motion, means for retaining the spherical-shaped object, the means being attached to the motor to rotate the spherical-shaped object, a stage attached to the motor and rotatable along the first axis, an arm extending from the stage, and a holder attached to the arm and rotatable along a second axis, the holder being removably coupled to the spherical-shaped object.

10. The system of claim 9 wherein the holder has at least one adjustable pin removably coupled to the spherical-shaped object.

11. The system of claim 10 wherein the at least one adjustable pin retains the spherical-shaped object by trapping the spherical-shaped object against another pin disposed in the holder.

12. An inspection device for retaining and rotating a spherical-shaped object, the device comprising:
- a housing;
- a motor attached to the housing for producing rotary motion;
- means for retaining the spherical-shaped object, the means being attached to the motor to rotate the spherical-shaped object;
- a stage attached to the motor and rotatable along a first axis;
- an arm extending from the stage; and
- a rod attached to the arm and rotatable along a second axis, the rod being removably coupled to the spherical-shaped object.

13. The device of claim 12 wherein the inspection device rotates the spherical-shaped object along a first and a second axis to allow an optical sensor to observe a portion of the surface of the spherical-shaped object.

14. The device of claim 12 wherein the rod is retained in a sleeve.

15. The device of claim 14 wherein the sleeve is flexible.

16. The device of claim 12 further comprising a holder attached to the motor and rotatable along a first axis, and having at least one adjustable pin rotatable along a second axis, the pin being removably coupled to the spherical-shaped object.

17. The device of claim 16 wherein the at least one adjustable pin retains the spherical-shaped object by trapping the spherical-shaped object against another pin disposed in the holder.

18. The device of claim 12 wherein the rod serves as a holder.

19. The device of claim 18 wherein the holder has at least one adjustable pin removably coupled to the spherical-shaped object.

20. The device of claim 19 wherein the at least one adjustable pin retains the spherical-shaped object by trapping the spherical-shaped object against another pin disposed in the holder.

21. An inspection device for retaining and rotating a spherical-shaped object, the device comprising:
- a housing;
- a motor attached to the housing for producing rotary motion;
- a stage attached to the motor and rotatable along a first axis;
- an arm extending from the stage; and
- a rod attached to the arm and rotatable along a second axis, the rod being removably coupled to the spherical-shaped object.

22. The device of claim 21 wherein the rod is retained in a sleeve.

23. The device of claim 22 wherein the rod is a hollow tube.

24. The device of claim 22 wherein the sleeve is flexible.

25. An inspection device for retaining and rotating a spherical-shaped object, the device comprising:
- a housing;
- a motor attached to the housing for producing rotary motion;
- a stage attached to the motor and rotatable along a first axis;
- an arm extending from the stage; and
- a holder attached to the arm and rotatable along a second axis, the holder being removably coupled to the spherical-shaped object.

26. The device of claim 25 wherein the holder has at least one adjustable pin removably coupled to the spherical-shaped object.

27. The device of claim 26 wherein the at least one adjustable pin retains the spherical-shaped object by trapping the spherical-shaped object against another pin disposed in the holder.

28. An inspection device for retaining and rotating a spherical-shaped object, the device comprising:
- a housing;
- a motor attached to the housing for producing rotary motion;
- means for retaining the spherical-shaped object, the means being attached to the motor to rotate the spherical-shaped object; and
- means for rotating the spherical-shaped object along a first and a second axis to allow an optical sensor to observe any and all portions of the surface of the spherical-shaped object.

* * * * *